United States Patent [19]
Jochim et al.

[11] Patent Number: 4,873,189
[45] Date of Patent: Oct. 10, 1989

[54] MONOCLONAL ANTIBODIES TO BLUETONGUE VIRUS ANTIGEN

[75] Inventors: Michael M. Jochim, Arvada; Suzanne C. Jones, Lakewood, both of Colo.

[73] Assignee: The United States of America as represented by the Secretary of Argriculture, Washington, D.C.

[21] Appl. No.: 570,155

[22] Filed: Jan. 12, 1984

[51] Int. Cl.[4] .................... C12P 21/00; C12N 15/00; C12N 5/00; C12Q 1/00
[52] U.S. Cl. ................... 435/68; 435/240.26; 435/240.27; 435/172.2; 435/7; 530/387; 935/103; 935/104; 935/108; 935/110; 436/548
[58] Field of Search ............ 435/68, 172.1, 240, 435/241, 948, 7, 240.26, 240.27; 260/112 R, 112 B; 436/548; 424/85; 530/387; 935/103, 104, 108, 110

[56] References Cited

U.S. PATENT DOCUMENTS 4,465,776  8/1984  Cidlowski et al. ................ 436/504

OTHER PUBLICATIONS

F. C. Thomas and D. O. Trainer, "Bluetongue Virus: Some Relationships Among North American Isolates and Further Comparisions with EHD Virus," *Can. J. Comp. Med.* 35:187–191 (1971).

H. Huismans, C. W. Bremer, and T. L. Barber, "The Nucleic Acid and Proteins of Epizootic Haemorrhagic Disease Virus," *Onderstepoort J. Vet. Res.* 46: 95–104 (1979).

J. R. White, A. M. Breschkin, and A. J. Della-Porta, "Immunochemical Analyses of Australian Blúetongue Virus Serotypes Using Monoclonal Antibodies," *Bluetongue and Related Orbiviruses*, Alan R. Liss, Inc., pp. 397–405 (1985).

M. J. Grubman, J. A. Appleton, and G. J. Letchworth, III, "Identification of Bluetongue Virus Type 17 Genome Segments Coding for Polypeptides Associated with Virus Neutralization and Intergroup Reactivity," *Virology* 131: 355–366 (1983).

J. A. Appleton and G. J. Letchworth, "Monoclonal Antibody Analysis of Serotype-Restricted and Unrestricted Bluetongue Viral Antigenic Determinants," *Virology*, vol. 124, pp. 286–299 (1983).

G. J. Letchworth and J. A. Appleton, "Heterogeneity of Neutralization -Related Epitopes within a Bluetongue Virus Serotype," *Virology*, vol. 124, pp. 300–307 (1983).

G. Köhler and C. Milstein, "Continuous Cultures of Fused Cells Secretina Antibody of Predefined Specificity," *Nature*, vol. 256, pp. 495–497 (1975).

G. Köhler and C. Milstein, "Derivation of Specific Antibody-Producing Tissue Culture and Tumor Lines by Cell Fusion," *European Journal of Immunology*, vol. 6, pp. 511–519 (1976).

G. Galfre, S. C. Howe and C. Milstein, "Antibodies to Major Histocompatibility Antigens Produced by Hybrid Cell Lines," *Nature*, vol. 266, pp. 550–552 (1977).

*Monoclonal Antibodies, Hybridomas: A New Dimension in Biological Analysis*, R. H. Kennett, T. J. McKearn, and K. B. Bechtol, Eds., Plenum Press, NY and London (1980).

M. Shulman, C. D. Wilde, and G. Köhler, "A Better Cell Line for Making Hybridomas Secreting Specific Antibodies," *Nature*, vol. 276, pp. 269–270 (1978).

M. M. Jochim, T. L. Barber, and B. M. Bando, "Identification of Bluetongue and Epizootic Hemorrhagic Disease Viruses by the Indirect Fluorescent Antibody Procedure," *Proceedings of the American Association of*

(List continued on next page.)

*Primary Examiner*—Robin L. Teskin
*Attorney, Agent, or Firm*—M. Howard Silverstein; Margaret A. Connor

[57] ABSTRACT

Hybrid cell lines which secret monoclonal antibody which is group-specific to bluetongue virus (BTV) antigen and which does not react to antigenically related epizootic hemorrhagic disease virus antigen are disclosed. The antibodies identify BTV in infected cell cultures with immunofluorescence and provide a means for ready diagnosis of BTV in animals.

12 Claims, 1 Drawing Sheet

OTHER PUBLICATIONS

*Veterinary Laboratory Diagnosticians*, pp. 91–103 (1974).

D. W. Verwoerd, H. J. Els, E. M. DeVilliers, and H. Huismans, "Structure of Bluetongue Virus Capsid," *Journal of Virology*, vol. 10, pp. 783–794 (1972).

M. M. Jochim and S. C. Jones, "Plaque Neutralization of Bluetongue Virus and Epizootic Hemorrhagic Disease Virus in $BHK_{21}$ Cells," *American Journal of Veterinary Research*, vol. 37, pp. 1345–1347 (1976).

*Selected Methods in Cellular Immunology*, B. B. Mishell and S. M. Shiigi, Eds., W. H. Freeman and Co., San Francisco, pp. 6–8 (1980).

R. H. Kennett, K. A. Denis, A. S. Tung, N. R. Klinman, "Hybrid Plasmacytoma Production: Fusions with Adult Spleen Cells, Monoclonal Spleen Fragments, Neonatal Spleen Cells and Human Spleen Cells," *Current Topics in Microbiological Immunology*, vol. 81, pp. 77–91 (1978).

Campbell et al., *Vet Microbiol*, vol 361, 1978 pp. 15–22 "Antigenic Relationship of Ibarakiving Bluetongue Virus and Epizootic Hemorrhagic Disease Virus".

Huismans et al., *Onaerstepoort T. Vet. Res.*, vol. 48, pp. 59–67, 1981.

Wiktor et al., *T. Virol Methods* vol. 1, pp. 33–46, 1980 "Use of Monoclonal Antibodies in the Diagnosis of Rabies Virus infection and Differentiation of Rabies and Rabies-Related Viruses".

MONOCLONAL ANTIBODIES TO BLUETONGUE VIRUS ANTIGEN

BACKGROUND OF THE INVENTION

The invention relates to a process for producing monoclonal antibodies to bluetongue virus antigen and to the hybrid cell lines that secrete these monospecific antibodies.

Bluetongue (BT) is an infectious, non-contagious, insect-transmitted virus disease that affects sheep, cattle, and other species of ruminant animals. Bluetongue virus (BTV) is classified as an orbivirus and is antigenically related to epizootic hemorrhagic disease virus (EHDV), also an orbivirus. Presently, 23 serotypes of BTV have been identified in the world and five serotypes are known to be present in the United States.

BTV infection in sheep is usually acute with a mortality rate in infected sheep of about 20–50%. Clinical symptoms of illness due to BTV are less apparent in cattle than in sheep and over 90% of BTVinfected cattle have mild or undetectable clinical signs of infection. However, infected cattle are important in the epizootiology of BT because cattle are often reservoirs of the virus. In addition, although BTV causes more direct losses in sheep production, significant economic losses result from BTV infections in cattle due to embargoes and restriction of export markets for cattle.

Proper treatment for BTV depends on accurate diagnosis of the disease. Problems in diagnosing BTV result, however, becuse EHDV, a closely related orbivirus, also infects cattle and produces a similar clinical syndrome. Because the two diseases are so similar it is necessary to isolate the viral agent and correctly identify it in order to facilitate an accurate diagnosis. One method that has been used to differentiate between BTV and EHDV is the indirect fluorescent antibody test (IFAT), which uses hyperimmune rabbit serum taken from BTV- or EHDV-inoculated rabbits to visualize viral antigen in virus-infected cell cultures. Because BTV and EHDV "share" antigenic sites on some of the polypeptides, even the most specific rabbit serum will contain antibodies that cross-react with viral antigens associated with both BTV and EHDV. Heretofore it has been necessary to dilute the cross-reacting antibody to a point where the serum became specific only for the homologous virus. However, there is always a possibility of incorrectly identifying BTV with this system. What has been needed to improve the capability of the diagnostic laboratory to differentiate between BTV and EHDV is an antibody that will identify BTV without cross-reacting with the antigenically related EHDV. In addition, because more than one serotype of BTV can be present in an infected animal and/or an infection outbreak area, it is highly desirable that such a BTV-specific antibody be group-specific, that is, would recognize any of the serotypes of BTV that might be present, rather than only be specific to one serotype. It is also desirable to have a method of visualizing BT viral-specific antigens in cell cultures.

The production of monoclonal antibodies by the fusion of spleen cells from immunized mice and myeloma cells grown in continuous culture, has been described previously, e.g., Kohler et al. in *Nature*, Vol. 256, pp. 495–497 (1975), Kohler et al. in *European Journal of Immunology*, Vol. 6, pp. 511–519 (1976), Galfre et al. in *Nature*, Vol. 266, pp. 550–552 (1977), and in the text *Monoclonal Antibodies, Hybridomas: A New Dimension in Biological Analysis*, R. Kennett, T. McKearn, K. Bechtol, Eds., Plenum Press, N.Y. and London, (1980). Techniques for the chemical selection of hybridomas arising from such a fusion, and subsequent isolation of single antibody secreting cell clones for the production of the monoclonal antibodies are also known. However, no cell lines have been produced capable of secreting monoclonal antibodies which are group-specific to BTV, rather than serotype-specific, which do not give false positive reactions to obiviruses such as EHDV, and which have been shown to be useful for identification of BTV antigens using simple tests such as immunofluorescence.

It should be noted that because of the unpredictable nature of hybrid cell preparation one cannot extrapolate from one antigen or cell system to another.

SUMMARY OF THE INVENTION

We have prepared hybrid cell lines which secret monoclonal antibodies to BTV which are group-specific rather than serotype-specific and which do not cross-react with closely related obiviruses such as EHDV. Because the novel antibodies produced by the hybridomas of our invention are group-specific, that is, react with polypeptides common to all serotypes of BTV as determined by tests against the five serotypes present in the United States, and do not recognize the antigenic determines associated with EHDV, BTV outbreaks can be readily and accurately diagnosed.

In addition, because the monoclonal antibodies of the invention identify BTV in infected cell cultures with immunofluorescence, they provide a means for ready diagnosis of BTV antigens using simple tests such as the IFAT.

In accordance with this discovery, it is an object of the invention to provide hybridomas which produce antibodies which are group-specific to BTV and do not react with EHDV.

It is also an object of the invention to provide methods for preparing these hybridomas.

It is a further object of the present invention to provide antibodies which react with a group-specific BTV viral antigen and do not recognize the antigenic determinants associated with EHDV and to provide methods of preparing these antibodies.

A still further object of the invention is to provide methods for ready identification and diagnosis of BTV and differentiation of this virus from other closely related orbiviruses using these antibodies, and to provide a method of visualizing BT viral-specific antigens in cell cultures.

Other objects and advantages of this invention will become readily apparent from the ensuing description.

DETAILED DESCRIPTION OF THE INVENTION

Figure 1:
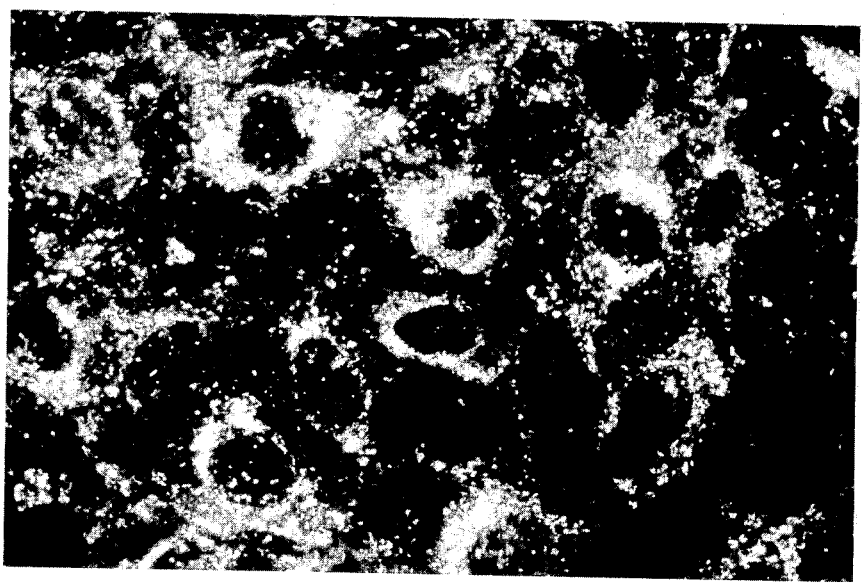
FIGS. 1-2 show immunofluorescent staining of monoclonal antibodies secreted by the hybrid cell lines of the invention.

The method of preparing the hybridomas comprises the following steps:

Mice are injected with bluetongue virus (BTV) to stimulate (immunize) the lymphocyte population to produce antibodies (immunoglobulins) to the viral antigens associated with the virus and the viral antigens associated with the replication of the virus in the animal. After a period of time and a series of injections the mice are stimulated one last time by intravenous inoculation of virus and 3 days later the spleens are removed for subsequent cell fusion experiments.

Next, myeloma cells that have the capability of continuous growth in cell culture medium and spleen cells that are secreting specific antibodies after stimulation, as described above, are fused to form hybrid cells (hybridomas) that have characteristics of the parental cells. Hybridomas are selected from the parental myeloma cells on the basis of the sensitivity of the myeloma cells to medium that contains hypoxanthine-aminopterin-thymidine (HAT). Myeloma cells useful for this invention lack the enzyme hypoxanthine phosphoribosyl transferase, and thus die in HAT selective medium. Exemplary myeloma cells for this invention are SP2/0-Ag14, which are derived from a hybrid that was produced from BALB/c spleen cells and X63-Ag8, a cell line frequently used to produce ybridomas as described by Shulman et al. in *Nature*, Vol. 276, pp. 269-270 (1978). In addition to their sensitivity to HAT medium these cells are resistant to 20 μg/ml of 8-azaguanine and synthesize no immunoglobulin. The advantage of fusing a non-immunoglobulin secreting myeloma cell is that any immunoglobulin associated with the growth of hybridomas arising from the fusion will indicate a contribution from the spleen cell.

The myeloma cells are maintained in suitable growth medium such as Dulbecco's Modified Eagle Medium that contains fetal bovine serum, 2-mercaptoethanol, and 8-azaguanine; incubation of cultures in this medium is at 37° C. under 7% $CO_2$ tension and 95% humidity. Cells are subcultured every day for 3 days prior to fusion.

Suitable techniques for cell fusion to obtain hybridomas are described in Kennett et al. in *Current Topics in Microbiological Immunology*, Vol. 81, pp 77-91, (1978) and *Monoclonal Antibodies, Hybridomas: A New Dimension in Biological Analysis*, R. Kennett, T. McKearn, K. Bechtol, Eds., Plenum Press, N.Y. & London (1980). Basically the spleen cells and the myeloma cells are fused in the presence of polyethylene glycol (PEG). Feeder cells such as mouse peritoneal macrophages can be added to the fusion mixture to aid in the establishment of hybridomas. The cell suspension is diluted in the appropriate medium and 50 μl added to each well of a 96-well cell culture plate. After 1 day of incubation at 37° C., under 5% $CO_2$ and 95% humidity, each well receives a drop of medium containing HAT to kill the myeloma cells while permitting growth of the hybrids. Small colonies of hybridomas can be seen within about 5 days after the fusion and when they are about 2 mm in diameter they can be transferred to new microplates using a pasteur pipette to transfer a single colony to an individual well. Hybridomas are propagated in medium containing HAT and the spent medium tested for the presence of immunoglobulin and for the presence of antibodies specific for the viral antigen of interest. A number of different serologic tests are known for evaluating the antibodies secreted by the various hybridomas. In the process of this invention, a preferred method of selecting hybridomas which secret the novel antibodies which react to group-specific BTV antigen determinants but not to EHDV antigen is on the basis of the reaction of antibody-containing hybridoma fluid in the indirect fluorescent antibody test (IFAT) using BTV-infected cell cultures and fluorescein isothiocyanate conjugated antimouse IgG to visualize the antigen-antibody reaction. Antibodies are selected which react with group-specific BTV antigen in the IFAT, do not react with EHDV antigen in the IFAT, and do not react with uninfected Vero cultured cells in the IFAT. This use of BT group-specific monoclonal antibody in the IFAT has not been disclosed previously. The IFAT is particularly useful because the antibody is monospecific for BTV only and cell cultures infected with EHDV will be obviously negative.

After unique hybridomas are identified they are cloned such as by limiting dilution techniques to establish, from a single hybridoma cell, antibody producing cell clones which can then be propagated indefinitely.

The group specificity of antibodies to BTV is determined by testing against each of the five serotypes of BTV present in the United States, namely, BTV serotypes 2, 10, 11, 13, and 17. Antibodies which react to all five serotypes are concluded to be reacting with polypeptides common to all serotypes of BTV, and are designated to be group-specific. Next, the antibodies are tested for reactivity to EHDV serotypes 1 and 2 which have been shown to cross-react with BTV in other tests. Antibodies which do not react with the two EHDV serotypes are designated as not recognizing the antigenic determinants associated with EHDV.

Two of the hybridomas obtained by the present invention are monoclones which secrete IgG antibody which reacts with viral antigen present in cell cultures infected with any of five serotypes of BTV present in the U.S. and does not react with cell cultures infected with either of two serotypes of EHDV (Serotype 1-New Jersey and Serotype 2-Alberta) which have been shown to cross-react in other serological tests for BTV. The monoclones are identified as BTV10XSP2/0-Ag14-10A1.34 and BTV10XSP2/0-Ag14-10D4.90. They have been deposited with the American Type Culture Collection, Rockville, MD, and have been assigned the designations HB 8219 and HB 8377, respectively.

Because of the specificity of the monoclonal antibodies produced by the cloned hybridomas for antigenic sites associated with BTV, they can be used to identify the presence of BTV antigen in infected cultured cells to diagnose bluetongue disease. Because the antibodies of the invention identify BTV with immunofluorescence, they can be used in the IFAT to provide a simple and accurate diagnostic test for BTV in animals. In such a diagnostic procedure, virus from the infected animal is isolated and adapted to grow in a cell culture. BTV is identified by applying the IFAT using monoclonal antibody of the invention which reacts with group-specific BTV antigen in the IFAT, does not react with EHDV antigen in the IFAT, and does not react with uninfected Vero cultured cells used in the IFAT, in combination with fluorescein isothiocyanate conjugated rabbit antimouse IgG. Next, the BTV antigenantibody complex is observed under ultraviolet light.

The antibodies of the invention can also be used to identify BTV antigens associated with infected tissues such as blood cells and histologic sections of organs taken from diseased animals. In either case the monoclonal antibodies can be used in combination with or coupled to an immunochemical such as fluorescein isothiocyanate, peroxidase, alkaline phosphatase or other such reagent. The antibody can also be used for development of "antigen capture" techniques whereby the antibody is first attached to a plastic substrate and then blood or tissure suspensions from infected animals are brought in contact with the antibody, which "captures the viral-antigen", and preserves it for subsequent identification. Because of the specificity of the antibody it can be used to differentiate BT virus from other closely related orbiviruses such as epizootic hemorrhagic disease virus.

EXAMPLE

The following example illustrates the present invention and is not intended to limit the same.

A. Preparation of BTV for Mouse Inoculation

The virus used to immunize mice was strain BT-8 (serotype 10) that had been partially purified by a modification described below of the procedure of Verwoerd et al. in *Journal of Virology,* Vol. 10(4) pp. 783–794 (1972). Monolayer cultures of BHK-21 cells in 690 $cm^2$ glass roller bottles were infected with the 12th cell culture passage of BT-8 and cells were harvested and separated from the culture fluid when 75% or more of the cells appeared infected. After centrifugation at 1500 g the cells were suspended in 0.002 M Tris-HC1 buffer (pH 8.8), using a volume equal to 1/80th of the volume of the original cell culture fluid. A 1% suspension of Sephadex G-200 (Pharmacia Laboratories Inc., Piscataway, NJ) in Tris buffer, was added at a tenth volume of the Tris buffer. Genesolv-D (trichlorotrifluoroethane, Allied Chemical Corp., Morristown, NJ) was then added at a third of the total volume. The mixture was shaken vigorously for 3 to 5 minutes and centrifuged at 200xg for 30 minutes. The supernate was removed and saved and the cells extracted a second time with fresh Tris buffer and Genesolv-D. The supernate from both extractions was pooled, diluted 1:1(v/v) with buffered lactose peptone, and stored at −70° C. The infectivity of the virus was determined by titration in BHK-21 cells as described by Jochim et al. in *American Journal of Veterinary Research,* Vol. 37, pp. 1345–1347 (1976).

B. Immunization of Mice

Adult, female, BALB/c mice were immunized by 2 intraperitoneal injections of $3.2\times10^6$ plaque forming units (PFU) of BTV, given approximately 5 weeks apart. After 2 weeks the mice were injected with $1.6\times10^6$ PFU of BTV intravenously (i.v.), rested 20 weeks, and reinjected i.v. with the same amount of virus as the previous i.v. injection.

C. Preparation of Spleen Cells for Fusion

The spleen cell suspension was prepared in the manner described by R. H. Kennett, "Fusion Protocols," in: *Monoclonal Antibodies, Hybridomas: A New Dimension in Biological Analyses,* R. Kennett, T. McKearn, K. Bechtol, Eds., Plenum Press, New York and London, pp. 365–367 (1980). Spleens were removed aseptically from immunized mice 3 days after the last injection of BTV and held in HY medium as formulated by Kennett. This medium consisted of Dulbecco's Modified Eagle Medium (with 4.5 g/liter of glucose and 4 mM glutamine) plus 10% NCTC 109 (Microbiological Associates, Los Angeles, CA), fetal bovine serum (20%) that had been screened for high cloning efficiency (Sterile Systems Inc, Logan, UT), oxaloacetate (0.15 mg/ml), pyruvate (0.05 mg/ml), bovine insulin (0.2 U/ml), penicillin (400 units ml), streptomycin (400μg/ml), and Fungizone (2 μg/ml). Cells were perfused from the spleens by injecting 15 ml of HY medium into the spleens through a 26-gauge needle. Red blood cells were lysed when 5 ml of ice-cold 0.17 M $NH_4Cl$ was added to the cell suspension and the cells were held on ice for 10 minutes. Cold HY medium was added, the cells pelleted at 300xg for 10 minutes and then resuspended in fresh HY medium for counting. Three spleens were perfused and approximately $2.8\times10^8$ cells were obtained.

D. Preparation of Myeloma Cells for Fusion

The myeloma cells, SP2/O-Ag14, were obtained from the Salk Institute for Biological Studies, San Diego, CA, and are described by Shulman et al. in *NATURE,* Vol. 276, pp. 269–270 (1978), as originating from a hybrid between a BALB/c spleen cell and the myeloma cell line X63-Ag8. The cells do not produce immunoglobulin and they die in a medium supplemented with HAT. Cells are maintained in Dulbecco's Modified Eagle medium with fetal bovine serum (10%), 2-mercaptoethanol ($10^{-5}$M) and 8-azaguanine (15 μg/ml) under 7% $CO_2$ at 37° C. Prior to the fusion, cells were subcultured each day for 3 days, removed from the culture dishes with a rubber policeman, pelleted by centrifugation at 300xg and resuspended in HY medium for counting.

E. Preparation of Peritoneal Macrophages

Macrophages are often used as feeder cells during the production of hybridomas. We used a method to stimulate the production of macrophages that was suggested in *Selected Methods in Cellular Immunology,* B. Mishell and S. Shiigi, Eds, W. H. Freeman and Co., San Francisco, pp. 6–8 (1980). BALB/c mice were inoculated intraperitoneally with 2 ml of 3% thioglycollate medium that had been held in the dark for several months. Six days after the injection, on the same day as the cell fusion, the mice were euthanized with chloroform. Macrophages were collected immediately by injecting the 5 ml of phosphate buffered saline, with 5 units/ml of heparin, into the peritoneal cavity, massaging the peritoneum, and withdrawing the fluid. Cells were pelleted at 600xg and resuspended in HY medium for counting.

F. Production of Hybrid Cells (Fusion Technique)

An amount of the spleen cell suspension which contained $1\times10^8$ cells was mixed with an amount of the myeloma cell suspension which contained $1\times10^7$ cells. After low speed centrifugation for 10 minutes at 300xg to pack the cells, they were washed once in serum-free HY medium and pelleted by centrifugation at 300xg for 10 minutes in a round-bottomed tube. The supernatant fluid was removed completely and the pellet loosened by tapping the tube. Next, 0.2 ml of 50%(w/v) polyethylene glycol 1000, prepared in serum free HY medium and warmed to 37° C., was added to the cells. The mixture was agitated gently, placed in the centrifuge within 2 minutes, and centrifuged at 300xg for 5½ minutes. The mixture was diluted gently with 5 ml of serum-free HY medium and then further diluted by 5 ml of Hy medium containing fetal bovine serum (20%). Cells were pelleted by centrifugation at 300 g for 10 minutes and the supernatant discarded. Cells were resuspended in 20 ml of HY medium containing hypoxanthine (13.6 μg/ml) and thymidine (7.6 μg/ml). An appropriate suspension of macrophages was pelleted and then resuspended in 10 ml of hypoxanthine-thymidine supplemented HY medium at a concentration of $1.02\times10^6$ cells/ml. This suspension was added to the fused-cell suspension, mixed gently and distributed into six 96 well flat-bottomed microplates at 50 μl of suspension per 6 mm-well. Plates were covered and held at 37° C. with 5% $CO_2$ and 95% humidity. The next day one drop of HY medium that contained hypoxanthine, aminopterin (0.18 μg/ml) and thymidine (HAT) was added to each well. About 7 days later small colonies of hybrids began to appear and when they reached 1.0–1.5 mm in diameter a capillary pipette was used to transfer cells from the center of such individual isolated colonies into a new 6 mm-well. During this time and the subsequent transfer of hybridomas for expansion into 16-mm wells the cells were maintained in HY-HAT medium.

G. Analysis of Hybridomas

The indirect fluorescent antibody test (IFAT) as described by Jochim et al. in *Proceedings of the American Association of Veterinary Laboratory Diagnosticians*, pp. 91–103 (1974), was used to evaluate spent culture fluids recovered from hybridomas transferred to and growing in 16 mm-wells. Undiluted fluids were tested on virus-infected, acetone-fixed monolayers of African green monkey kidney (Vero) cells grown in 8-chambered slides (Miles Laboratories, Inc, Naperville, IL). Fluorescein isothiocyanate (FITC)-labeled rabbit anti-mouse IgG, (Miles Laboratories, Inc., Elkhart, IN) was added to the primary antigen-antibody reaction in order to visualize the antigen with reflected light fluorescence microscopy. Fluids of interest were tested on cells infected with the homologous serotype 10 virus (strain BT-8) as well as heterologous BTV-serotypes 2, 11, 13, 17, represented by strains BT-Ona, BT-Station, 67-41B and 62-45S, respectively. Also, epizootic hemorrhagic disease virus (EHDV) serotypes 1 and 2, represented by strains New Jersey and Alberta, were included to evaluate the presence of cross-reactive antibodies to this antigenically related orbivirus. Controls for the test included uninfected Vero cells and BTV- or EHDV-infected Vero cells that were reacted with antibody from rabbits given multiple injections of either BTV or EHDV, and visualized with FITC-labeled goat anti-rabbit IgG (Miles Laboratories, Inc., Elkhart, IN).

Of the 115 hybridomas that were identified microscopically and transferred from the original 6 mm-wells, there were 84 that continued to grow in the new wells. However, only 52 of the heartiest hybridomas were selected to be tested by IFAT and 14 of these were positive against the homologous virus in BTV-infected Vero cell cultures. When culture fluids from these IFAT-positive hybridomas were tested against EHDV-infected Vero cell cultures, ten did not react; four reacted with antigenic determinants that apparently are shared by these two distinct orbiviruses. Two hybridomas, identified as 10A1 and 10D4, and show to secrete antibody to the homologous BT viral antigen were tested further by the IFAT with Vero cells infected with the other four serotypes of BTV. Antibody secreted by hybridoma 10A1 and 10D4 was BTV-group specific in the IFAT, as there was little difference in the strain characteristics among the Vero cells infected with the five different serotypes. These staining characteristics were in sharp contrast to the immunofluorescence observed with hybridoma fluids that reacted with both BTV- and EHDV-infected Vero cell cultures. One hybridoma, identified as 10B4, secreted antibody that recognized the same antigenic determinant on viral antigens associated with both BTV- and EHDV-infected Vero cells. Cells from each of the IFAT positive hybridomas were frozen in growth medium that contained fetal bovine serum (20%) and dimethylsulfoxide (10%). Subsequently several hybridomas of interest were retrieved from liquid nitrogen storage and cloned to produce colonies of single antibody secreting cells.

H. Cloning of Hybridomas

In an effort to assure that the antibody secreted by a hybridoma is in fact monospecific it is necessary to disperse the population of cells so that a cell line can be established from a single cell. The method used here was that of limiting dilution and it was used to clone the hybridomas 10A1, 10B4, and 10D4. First the hybridomas were harvested, pelleted by low speed centrifugation, resuspended in HY-HAT medium and counted to determined the number of live cells. Then, 5 ml cell suspensions were made that each contained 10, 100, and 1,000 cells per ml and 50 μl amounts of such a suspension added to 200 μl of HY-HAT medium in each well of a 96-well flat-bottomed microplate. Cell cultures were held at 37° C. under 6% $CO_2$ and 95% humidity and observed each day for evidence of a single colony of cells that appeared to develop from a single cell. When a single colony in one well was about 2.0 mm in diameter the entire contents of the well was expanded to a new 6 mm-well and then to a 16 mm-well. Spent culture fluids were tested as previously described for the hybridomas cultures.

I. Analysis of Clones

There were 21 clones isolated from hybridomas 10A1 and they were maintained for several weeks in HY-HAT medium, which was recovered every 3–4 days and fresh medium added so that the antibody could be tested by the IFAT. Eighteen of these 10A1 clones were positive with BTV-infected Vero cells and did not reacted with EHDV-infected cells. Culture fluid from one particular clone, 10A1.34, yielded an especially strong response with the IFAT. Antibody from this clone was tested against each of the five serotypes of BTV present in the United States, i.e., BTV types 2, 10, 11, 13, and 17 and was found to react with all of the five serotypes. It was then tested against cell cultures infected with either of two serotypes of EHDV (Serotype 1-New Jersey and Serotype 2-Alberta) which have been shown to cross-react with in other tests for bluetongue. The monoclone was found not to react to either of the EHDV serotypes. The clone was expanded for growth in larger cell culture dishes and then adapted to grow in serum-free medium.

There were eight clones derived from hybridoma 10B4 and each was tested by the IFAT as described above. All of the clones reacted with both BTV and EHDV-infected Vero cells. Clones 10B4.183 was representative of the clones established from hybridoma 10B4 and was selected for further study because of the intense staining reaction in the IFAT.

There were seven clones isolated from hybridoma 10D4 and six of these were positive when tested by the IFAT. Like the 10A1 clones the 10D4 clones secreted antibody that reacted with BTV-antigen but did not react with EHDV-antigen. Clone 10D4.90 was representative of the clones derived from 10D4 and was characterized and compared to the other cloned hybridomas and similar to clone 10A1.34 it reacted with all of the five BTV serotypes but not with the EDV serotypes.

Figure 2:
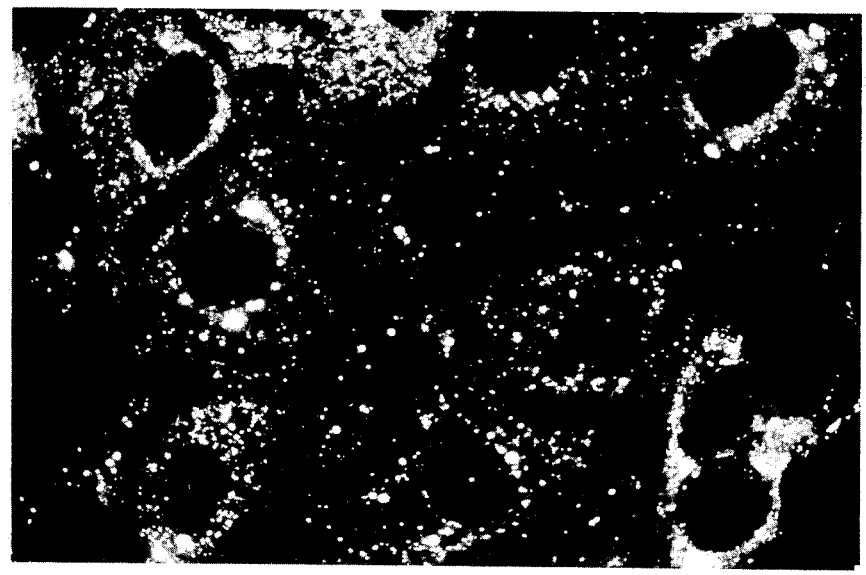

Obvious differences were observed in the immunofluorescent staining characteristic of the three clones, 10A1.34, 10B4.183, and 10D4.90. In the case of BTV-specific clone, 10A1.34, the antigen was diffuse and abundant throughout the cytoplasma of the cell; because the cytoplasm had shrunken somewhat during fixation and staining the antigen appeared to almost completely surround the nucleus and fill the cytoplasm (FIG. 1). In contrast to this pattern of staining, the antibody secreted by clone 10B4.183 reacted with antigen associated with spherical "inclusions" scattered throughout the cytoplasm of BTV-infected cells. When this antibody was used to stain EHDV-infected cells the pattern was unlike BTV-infected cells in that the fluorescent material was more irregular in shape. No fluorescent material was seen when antibody from clone 10A1.34 was tested on EHDV-infected cells. The cytoplasma of BTV-infected cells was filled with both large and small discrete granules and spherical inclusions when antibody from clone 10D4.90 was used in the IFAT (FIG. 2). Unlike clone 10B4.183, but similar to clone 10A1.34, this reaction was specific for BTV-infected cells. No fluorescence was seen when antibody from clone 10D4.90 was applied to EHDV-infected cells. Table I summarizes the results of these three distinct clones in the IFAT.

TABLE I

Results of the indirect fluorescent antibody test with three monoclonal antibodies

| Clone | BTV-infected cells | EHDV-infected cells |
| --- | --- | --- |
| 10A1.34 | +; diffuse cytoplasmic fluorescence | —; no staining of viral antigen |
| 10B4.183 | +; discrete spherical "inclusions" in cytoplasm | +; irregular shaped "inclusion" in cytoplasm. |
| 10D4.90 | +; abundant discrete granules and large and small spherical inclusions in cytoplasm | —; no staining of viral antigen |

J. Adaption of Hybridoma to Serum-free Medium

It may be advantageous to propagate monoclonal antibody producing cells in a medium that does not contain fetal bovine serum so that the antibody can be more easily isolated or concentrated. Clone 10A1.34 was adapted to grow in HB101 medium (Hana Media, Inc., Berkeley, CA) without fetal bovine serum as a supplement. The cells were first changed from HY medium with fetal bovine serum (20%) to HB101 medium with the same concentration of serum. During the next 6 to 8 weeks the serum concentration was reduced 2-fold every 3 to 7 days until the cells were growing in serum-free HB101 medium.

K. Production of Ascites in Histocompatible Mice

Clone 10A1.34 and 10D4.90 were shown to stimulate the production of ascites in histocompatible BALB/c mice. Adult female mice were stimulated by an intraperitoneal injection of 0.5 ml of pristane (2,6,10,14-Tetramethylpentadecane; Aldrich Chemical Co., Inc., Milwaukee, WI). Six weeks later each mouse was inoculated with $1 \times 10^5$ cells in 0.5 ml serum-free medium and 2 weeks later the first of several mls of ascitic fluid was recovered using an 18 guage needle. Although the ascitic fluid was not titered to determine the monoclonal antibody concentration we observed 4+ fluorescence, on a scale of 1 to 4, with the fluid diluted 1:40 and tested in the IFAT as previously described. This was at least 10 fold higher than the concentration of antibody in culture fluid.

L. Characterization of Immunoglobulin

The isotype of the immunoglobulin secreted by clones 10A1.34 and 10D4.90 was determined by immunodiffusion in agarose. Culture fluid from the clones was added to 4.0 mm-wells that were punched in the agarose in a pattern that consisted of a center well and 6 outside wells. The center well, also 4.0 mm in diameter and 2.0 mm from the outside wells (edge to edge) was filled with rabbit anti-mouse IgG1, IgG2a, or IgG2b (Miles Laboratories, Inc., Elkhart, IN). Precipitin lines that developed within 24 hrs were as follows: With clone 10A1.34 against anti-mouse IgG2b, and with clone 10D4.90 against IgG2a.

M. Cytogenetics of Myeloma and Cloned Hybridoma Cells

The SP2/0-Ag14 myeloma cell line and the 10A1.34 cloned hybridoma were examined by Dr. Ward D. Peterson, Jr., Childrens Hospital of Michigan, Detroit, MI, and the chromosome ploidy distribution was determined. Of the 100 metaphases examined for SP2/0-Ag14 cells, there were 97 with more than 70 chromosomes and 3 with more than 140. The exact chromosome count of 15 metaphases yielded a mean of 74 chromosomes. The diploid number of chromosomes for mouse is 2N=40 and all normal mouse chromosomes are acrcentric. The presence of metacentrics indicated that a fusion had occurred between 2 acrocentrics and in this cell line 1 to 6 metacentrics were found in the 15 metaphases examined. Most of the metaphases had 3 or 4 metacentrics per metaphase. The chromosome distribution of SP2/0-Ag14 had previously been reported by Shulman et al. in *Nature*, Vol. 276, pp. 269–270 (1978), to be "about 73". Hybridoma clone 10A1.34 was shown to have 91 metaphases with more than 100 chromosomes and 9 with more than 200. The exact chromosome count of 15 metaphases yielded a mean of 99 chromosomes which supports the evidence that fusion had occurred. The parental metacentric marker chromosomes were also present; 2 in 7 of 15 metaphases and 3 in 8 of 15 metaphases.

Having thus described our invention, we claim:

1. A hybridoma which secretes monoclonal antibody which is group-specific to bluetongue virus (BTV) antigen and does not cross react with epizootic hemorrhage disease virus (EHDV) antigen selected from the group consisting of ATCC HB 8219 and ATCC HB 8377.

2. A method of preparing monoclonal antibody which reacts with BTV antigen but not with EHDV antigen which comprises recovering antibody produced by the hybridomas of claim 1 by a method selected from the group consisting of (i) culturing said hybridoma in a medium and recovering the antibody from said medium, and (ii) culturing said hybridoma intraperitoneally in mice and harvesting malignant ascites or serum from said mice, which ascites or serum contains said antibody.

3. The monoclonal antibody prepared according to the method of claim 2.

4. A method of producing a hybridoma which secretes monoclonal antibody which is group-specfic to bluetongue virus (BTV) antigen and does not react with epizootic hemorrhagic disease virus (EHDV) antigen, which comprises:

(a) immunizing a mouse with BTV as follows: injecting said mouse with 2 intraperitoneal injections of $3.2 \times 10^6$ plague forming units (PFU) of BTV, given approximately 5 weeks apart; after 2 weeks, injecting said mouse with $1.6 \times 10^6$ PFU of BTV intravenously; resting said mouse 20 weeks and reinjecting it with $1.6 \times 10^6$ PFU of BTV intravenously;

(b) removing the spleen from said mouse 3 days after the last injection of BTV and making a suspension of the spleen cells;

(c) fusing said spleen cells, in the presence of a fusion promotor, with mouse myeloma cells which lack hypoxanthine phosphoribosyl transferase to form hybridomas capable of producing monoclonal antibody;

(d) individually culturing said hybridomas in a medium which will support growth of only said hybridomas so that said monoclonal antibody is secreted into said culture medium;

(e) testing said antibody-containing medium for the presence of antibody which is group-specific to BTV antigen and does not react with EHDV antigen as follows:

(i)(a) reacting said antibody-containing medium with cell cultures infected with BTV serotypes 2, 10, 11, 13, and 17;

(i)(b) reacting said antibody-containing medium with cell cultures infected with EHDV serotypes 1 and 2, and (i)(c) reacting said antibody-containing medium with uninfected cell cultures;

(ii) reacting said reacted cultures of step (i) with fluorescein isothiocyanate conjugated antimouse IgG;

(iii) observing said reacted cultures of step (ii) using fluorescent light microscopy; and (iv) selecting said antibody-containing medium in which said BTV-infected cultures show fluorescence in step (iii); said EHDV-infected cultures show no fluorescence in step (iii), and said uninfected cell cultures show no fluorescence in step (iii);

(f) cloning said hybridoma which is contained in said medium selected in step (e)(iv).

5. The hybridoma produced according to the method of claim 4.

6. The method of claim 4 which further includes:

(g) recovering said monoclonal antibody secreted by said hybridoma of step (f) by a method selected from the group consisting of (i) culturing said cloned hybridoma in a medium and recovering said antibody from said medium, and (ii) culturing said cloned hybridoma intraperitoneally in mice and harvesting malignant ascites or serum from said mice, which ascites or serum contains said antibody.

7. The monoclonal antibody produced according to the method of claim 6.

8. The monoclonal antibody of claim 7 in combination with immunochemicals.

9. The hybridoma prepared according to claim 4 formed by the fusion of SP2/0-Ag14 mouse myeloma cells and spleen cells from a mouse immunized with BTV serotype 10 (strain BT-8).

10. A method of diagnosing BTV in animals without the occurrence of false positive reactions to EHDV, which comprises:

(a) isolating virus from an infected animal to be diagnosed;

(b) growing said isolated virus in cell culture; and (c) identifying BTV in said isolated virus as BTV by applying the indirect fluorescent antibody test (IFAT) using monoclonal antibody produced according to the method of claim 4 which reacts to BTV antigen of serotypes 2, 10, 11, 13, and 17 as shown by the IFAT, does not react to EHDV antigen of serotypes 1 and 2 as shown by the IFAT, and does not react with uninfected cell cultures used in the IFAT, in combination with fluorescein isothiocyanate conjugated rabbit antimouse IgG, observing the BTV antigen-antibody complex under ultraviolet light; and identifying BTV-infected cells by the presence of fluorescent granules and spherical inclusions in the cytoplasm.

11. The method of claim 10 wherein said monoclonal antibody is produced by a hybridoma selected from the group consisting of ATCC HB 8219 and ATCC HB 8377.

12. A method of producing a hybridoma which secretes monoclonal antibody which is group specific to bluetongue virus (BTV) antigen and does not react with epizootic hemorrhagic disease virus (EHDV) antigen, comprising immunizing a mouse with BTV as follows: injecting said mouse with 2 intraperitoneal injections of $3.2 \times 10^6$ plague forming units (PFU) of BTV, given approximately 5 weeks apart; after 2 weeks, injecting said mouse with $1.6 \times 10^6$ PFU of BTV intravenously; resting said mouse 20 weeks and reinjecting it with $1.6 \times 10^6$ PFU of BTV intravenously; removing the spleen from said mouse 3 days after the last injection of BTV; and thereafter fusing cells from said spleen with mouse myeloma cells.

* * * * *